United States Patent [19]

VandenBerg

[11] Patent Number: Plant 7,602

[45] Date of Patent: Jul. 23, 1991

[54] CHRYSANTHEMUM PLANT NAMED PINK CARICIA

[75] Inventor: Cornelis P. VandenBerg, Salinas, Calif.

[73] Assignee: Yoder Brothers, Inc., Barberton, Ohio

[21] Appl. No.: 435,821

[22] Filed: Nov. 14, 1989

[51] Int. Cl.[5] ..... A01H 5/00

[52] U.S. Cl. ..... Plt./74

[58] Field of Search ..... Plt./74; 47/58; 800/200

[56] References Cited

U.S. PATENT DOCUMENTS

P.P. 6,902 7/1989 VandenBerg ..... Plt./74

4,616,099 10/1986 Sparkes ..... 47/58

OTHER PUBLICATIONS

Searle, S. A. et al., "Breeding and Selection"; Appendix I *Chrysanthemums the Year Round,* Blandford Press, London, 1968, pp. 26–29, 320–327.

Gosling, S. G., "Appendix II Sporting and Irradiation" *The Chrysanthemum Manuals* Nat. Chrysanth. Soc., London 1979, pp. 329–336.

*Primary Examiner*—James R. Feyrer

*Attorney, Agent, or Firm*—Foley & Lardner

[57] ABSTRACT

A Chrysanthemum plant named Pink Caricia particularly characterized by its flat capitulum form; anemone capitulum type; soft purple ray floret color; diameter across face of capitulum of up to 7 cm at maturity, and diameter of anemone cushion of up to 22 mm; uniform eight week photoperiodic flowering response to short days; peduncle length ranging from 8 to 18 cm on open, terminal sprays; medium plant height when grown as a single stem spray cut mum; and excellent tolerance to low temperatures for bud initiation and flower development.

1 Drawing Sheet

The present invention comprises a new and distinct cultivar of chrysanthemum, botanically known as *Dendranthema grandiflora,* and referred to by the cultivar name Pink Caricia.

Pink Caricia, identified as 84-567D01, is a product of a mutation induction program which had the objective of creating new Chrysanthemum cultivars that would expand the color range of an existing cultivar while retaining all other traits.

Pink Caricia was discovered and selected by Cornelis P. VandenBerg on Nov. 17, 1987 in a controlled environment in Salinas Calif. as one flowering plant within a flowering block established as rooted cuttings from stock plants which had been exposed as unrooted cuttings to an X-ray source of 1500 rads. The irradiated parent was the cultivar identified as Caricia, disclosed in plant patent application Ser. No. 187,654, now U.S. Plant Pat. No. 6,902.

The first act of asexual reproduction of Pink Caricia was accomplished when vegetative cuttings were taken from the initial selection in January 1988 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Pink Caricia are firmly fixed and are retained through successive generations of asexual reproduction.

Pink Caricia has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Pink Caricia, which, in combination, distinguish this Chrysanthemum as a new and distinct cultivar:

1. Flat capitulum form.
2. Anemone capitulum type.
3. Soft purple ray floret color.
4. Diameter across face of capitulum of up to 7 cm at maturity, with diameter of anemone cushion up to 22 mm.
5. Uniform eight week photoperiodic flowering response to short days.
6. Peduncle length ranging from 8 to 18 cm on open, terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawing shows typical inflorescence and leaf characteristics of Pink Caricia, with the colors being as nearly true as possible with illustrations of this type. The color photograph is a perspective view of Pink Caricia grown as a single stem cut spray mum.

Of the commercial cultivars known to the inventor, the most similar in comparison to Pink Caricia are the parent cultivar Caricia and the induced mutation White Caricia, created through the same mutation induction program as Pink Caricia, and disclosed in applicant's pending application Ser. No. 07/436,029, filed simultaneously with the present application. All traits of Pink Caricia are similar to those of Caricia and White Caricia, except the color of the ray florets. The color of the ray florets of Pink Caricia is significantly darker than the very soft pink color of the ray florets of Caricia, while the ray florets of White Caricia are white.

In the following description color references are made to The Royal Horticultural Society Colour Chart. The color values were determined on plant material grown as a single stem cut spray mum in Salinas, Calif. on July 13, 1989.

Classification:

*Botanical.*—*Dendranthema grandiflora* cv Pink Caricia.

*Commercial.*—Anemone cut spray mum.

INFLORESCENCE

A. Capitulum:

*Form.*—Flat.

*Type.*—Anemone.

*Diameter across face.*—Up to 7 cm at maturity.

*Diameter of anemone cushion.*—Up to 22 mm.

B. Corolla of ray florets:

*Color (general tonality from a distance of three meters).*—Light purple.

*Color (upper surface).*75C to 75D.

*Color (under surface).*—Almost white, with overcast of 75D.

*Shape.*—Flat, oblong.

C. Corolla of disc florets:

*Color (mature).*—155C, with tips of anemone disc florets 6A to 6B. The anemone florets are not at their fully mature stage in the photograph, with the mature color being visible only at the periphery of certain of the discs.

*Color (immature).*—Closest to 144B to 145A.

D. Reproductive Organs:

*Androecium.*—Present on disc florets only; scant pollen.

*Gynoecium.*—Present on both ray and disc florets.

PLANT

A. General appearance:

*Height.*—Medium; 90 to 100 cm as a single stem cut mum with two long day weeks prior to short days.

Foliage:

*Color (upper surface).*—147A.

*Color (under surface).*—147B.

*Shape.*—Lobed and slightly serrated.

I claim:

1. A new and distinct Chrysanthemum plant named Pink Caricia, as described and illustrated.

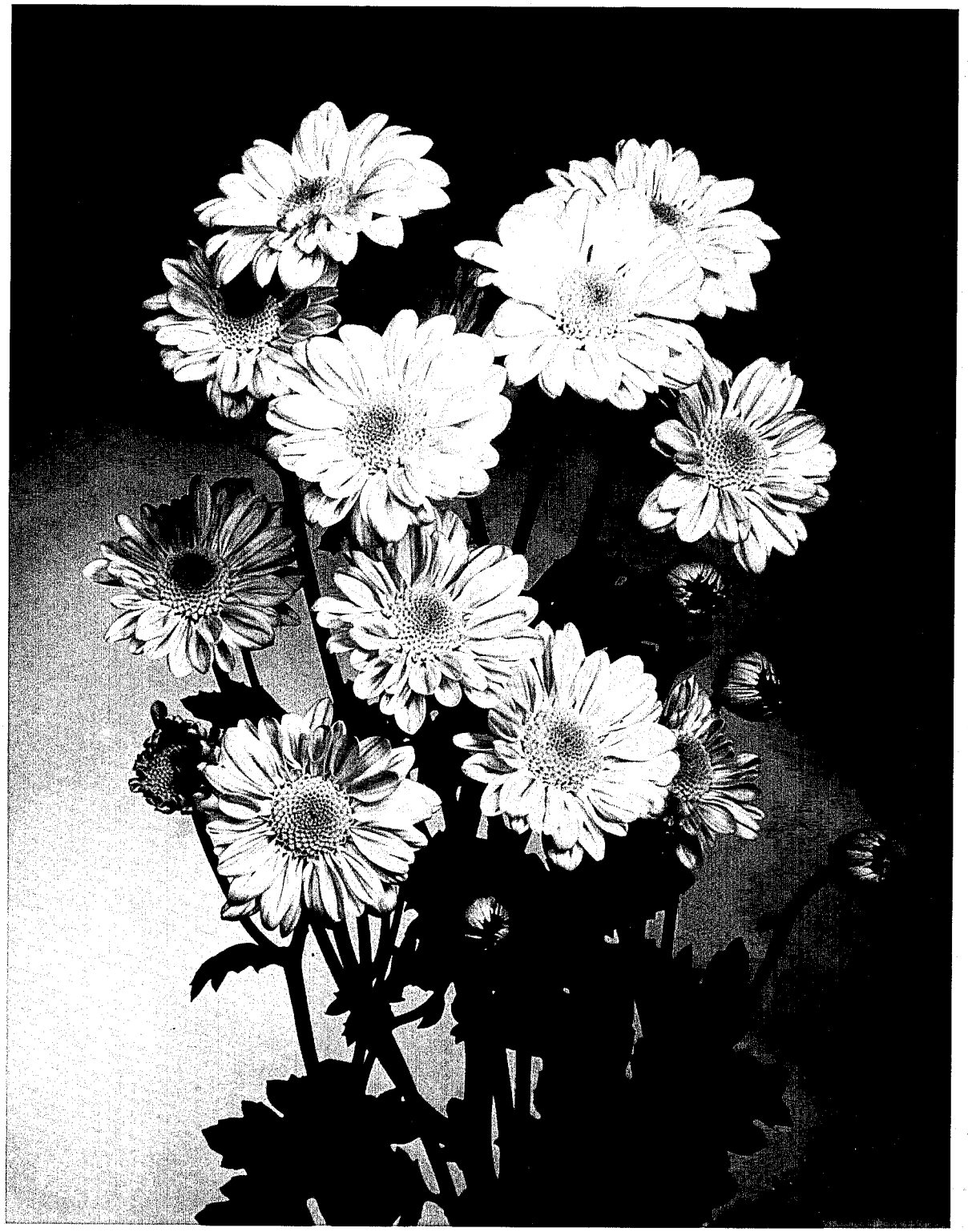

* * * * *